United States Patent [19]

Leary et al.

[11] 4,263,508
[45] Apr. 21, 1981

[54] PULSE EDGE MEASUREMENT FOR DETERMINING PARTICLE DIMENSIONAL CHARACTERISTICS

[75] Inventors: James F. Leary, Rochester, N.Y.; Paul Todd, State College, Pa.

[73] Assignee: Research Corporation, New York, N.Y.

[21] Appl. No.: 31,928

[22] Filed: Apr. 20, 1979

[51] Int. Cl.³ .................... G01N 23/00; G01N 21/64; G01N 15/02
[52] U.S. Cl. .......................... 250/358 R; 250/461 B; 356/335
[58] Field of Search ........... 250/358 R, 461 R, 461 B, 250/222 PC; 324/71 CP, 102, 181; 356/335, 336

[56] References Cited

U.S. PATENT DOCUMENTS

| | | | |
|---|---|---|---|
| 2,656,508 | 10/1953 | Coulter | 324/71 CP |
| 3,327,117 | 6/1967 | Kamentsky | 250/461 R |
| 3,532,905 | 12/1967 | Zijta et al. | 307/265 |
| 3,657,537 | 4/1972 | Wheeless, Jr. et al. | 250/461 R |
| 3,701,029 | 10/1972 | Hogg | 324/71 CP |
| 3,703,641 | 11/1972 | Rosen | 250/574 |
| 3,710,933 | 1/1973 | Fulwyler et al. | 324/71 CP |
| 3,735,261 | 5/1973 | Vahlstrom et al. | 324/181 |
| 3,770,349 | 11/1973 | Legorreta-Sanchez | 356/73 |
| 3,781,674 | 12/1973 | Claps | 324/71 CP |
| 3,851,169 | 11/1974 | Faxvog | 250/222 PC |
| 3,919,050 | 11/1975 | Curby | 324/71 CP |
| 3,961,249 | 6/1976 | Coulter | 324/71 CP |
| 3,963,983 | 6/1976 | Hogg | 324/71 CP |

OTHER PUBLICATIONS

L. L. Wheeless, Jr. and S. F. Patten, Jr., "Slit-Scan Cytofluorometry", Acta Cytol., vol. 17, No. 4, pp. 333-339 (1973).
L. L. Wheeless, Jr., A. Hardy and N. Balasubramanian, "Slit-Scan Flow System for Automated Cytopathology", Acta Cytol., vol. 19, No. 1, pp. 45-52 (1975).
T. K. Sharpless and M. R. Melamed, "Estimation of Cell Size from Pulse Shape in Flow Cytofluorometry", J. Histochem. Cytochem., vol. 24, No. 1, pp. 257-264 (1976).
J. F. Leary, P. Todd, J. C. S. Wood, and J. H. Jett, "Laser Flow Cytometric Light Scatter and Fluorescence Pulse-Width and Pulse Rise-Time Sizing of Mammalian Cells", J. Cytochem., Cytochem., vol. 27, No. 1, pp. 315-320 (1979).

Primary Examiner—Alfred E. Smith
Assistant Examiner—Janice A. Howell
Attorney, Agent, or Firm—Kerkam, Stowell, Kondracki & Clarke

[57] ABSTRACT

Method and apparatus for analyzing pulses from optical devices such as flow cytometers to generate indicators of particle dimensional attributes, such as size and shape, as well as orientations in a flow stream of non-spherical particles. Particles are conveyed through a beam of electromagnetic radiation and a photodetector responds to radiation resulting from interaction of the particle with the beam to output a resultant signal in the form of a pulse as a particle enters and passes through the beam. Pulse edge width between two threshold values, preferably established as constant fractions of peak pulse amplitude, is measured as an indication of a particle dimensional attribute.

41 Claims, 9 Drawing Figures

LASER BEAM INTENSITY PROFILE

FLOW DIRECTION AT CONSTANT VELOCITY

DETECTOR RESPONSE AS FUNCTION OF TIME

FIG. 3

IMAGE * APERTURE + NOISE = PULSE

FIG. 6 (PRIOR ART)
PULSE WIDTH SIZING OF MICROSPHERES

FIG. 5

FIG. 7 RISE-TIME SIZING UP MICROSPHERES

FIG. 9

PULSE EDGE MEASUREMENT FOR DETERMINING PARTICLE DIMENSIONAL CHARACTERISTICS

Support for this invention was received through U.S. Public Health Service Contract Nos. NO1-CB-43984 and NO1-CB-74171, and grant RO1-CA-17536.

BACKGROUND OF THE INVENTION

The present invention generally relates to sizing of particles, for example biological cells and related biological particles such as nuclei, chromosomes and other sub-cellular organelles, through analysis of signal pulses from either fluorescence or light scatter in flow cytometers or similar flow meters, and, more particularly, relates to methods and apparatus for differentiating particles of different size, shape or orientation from one another.

FLow cytometers and similar devices for measuring particle characteristics, not limited to biological particles, generally operate by conveying particles one-by-one through a beam of exciting electromagnetic radiation, for example from a laser, and responding to radiation resulting from interaction of the particle with the beam to output a signal in the form of a pulse as the particle enters and passes through the beam. Two examples of radiation resulting from interaction of the particle with the beam are scattered light and secondary fluorescence.

There is presently an interest in the accurate sizing of live biological cells both for clinically useful applications, and for the answering of important questions in cell biology. Accordingly, a number of approaches have been proposed for determining cell size non-destructively employing flow cytometers.

One approach to determining cell size has been to use intensities of light scattered at small angles. The intensity of light scattered in the near forward direction is predominantly due to diffraction (first ring of the diffraction pattern) and is roughly proportional to the cross-sectional area of the cell. There are, however, a number of problems with this light scatter approach. For one, the angular width of the first ring of the diffraction pattern decreases with increasing cell size. Another problem is that the use of laser beam dumps or obscuration bars in commercial flow cytometers modifies the proportion of the scattered light which reaches the detectors, thereby leading to a non-systematic relationship between scattered light intensity and cell cross-sectional area. A third problem is that at angles greater than those subtended by the main diffraction ring from the cell, typically 2° to 3° for most mammalian cells, the scattered light intensity is strongly dependent on cell refractive index. Two cells of the same size but of different refractive index, sometimes reflecting changes in internal cell structure, will have different light scattering intensities. Light scatter intensity in the above-described approach is thus not always a reliable measure of cell size.

A different approach to sizing of live biological cells, and more particularly to determining nuclear to cytoplasmic (N/C) ratio, is a "slit-scan" or "programmed pulse shape analysis" technique whereby the fluorescence pulse shapes of Acridine Orange metachromatically stained cells passing through a slit focused laser beam (typically five micrometers in width) are subsequently analyzed by a level detection algorithm which defines the nuclear boundary, thereby enabling nuclear-to-cell size measurements to be determined on a cell-by-cell basis. This technique is described in the Wheeless, Jr., et al U.S. Pat. No. 3,657,537, and in the following two literature references: L. L. Wheeless, Jr. and S. F. Patten, Jr., "Slit-Scan Cytofluorometry", *Acta Cytol.*, Vol. 17, No. 4, pp. 333–339 (1973); and L. L. Wheeless, Jr., A. Hardy and N. Balasubramanian, "Slit-Scan Flow System for Automated Cytopathology", *Acta Cytol.*, Vol. 19, No. 1, pp. 45–52 (1975).

Another sizing technique is described in the Coulter U.S. Pat. No. 3,961,249 which discloses a particle size analyzer responding to output pulses from apparatuus such as is disclosed in the Coulter U.S. Pat. No. 2,656,508 utilizing what is known as the Coulter principle. As is pointed out in the Coulter U.S. Pat. No. 3,961,249, the amplitude of a Coulter pulse is an indicator of cell or particle size. It is pointed out in this Coulter U.S. Pat. No. 3,961,249 that another indication of particle size may be obtained by differentiating one of the edges of the Coulter counter particle pulse, preferably the trailing edge. Specifically, the peak value of the derivative is an indicator of particle size.

Another prior art sizing technique may be generally termed "time-of-flight" wherein output pulse width of a cytometer is measured, with the pulse resulting either from fluorescence or light scatter. Various specific time-of-flight measurement techniques are described in the literature reference: T. K. Sharpless and M. R. Melamed, "Estimation of Cell Size From Pulse Shape in FLow Cytofluorometry", *J. Histochem. Cytochem.*, Vol. 24, No. 1, pp. 257–264 (1976). It should be pointed out that the present invention is specifically directed to new apparatus and new methods for analyzing previously known signal pulses similar to those pulses described in the above cited Sharpless and Melamed article. Accordingly, to the extent that the Sharpless and Melamed article is useful for understanding the nature of cytometer pulses and the manner in which they are obtained, the entire disclosure of the above cited Sharpless and Melamed article entitled "Estimation of Cell Size From Pulse Shape in Flow Cytofluorometry" is hereby expressly incorporated by reference. However, the particular methods and apparatus by which these pulses are analyzed according to the present invention to yield size information are not disclosed in the Sharpless and Melamed article, and there are corresponding details of these signal pulses which, although present in the actual pulses, are not described in the Sharpless and Melamed article.

As described in the Sharpless and Melamed article, cytometer output pulses can be analyzed in various ways to provide particle size estimates.

As Sharpless and Melamed point out, the most straightforward approach would be to measure overall pulse width employing a threshold level set just high enough to exclude background noise. Measured pulse width then corresponds to that portion of the pulse which begins where pulse amplitude crosses the threshold level on the rising edge of the pulse, and ends where pulse amplitude re-crosses the threshold level on the falling edge of the pulse. One drawback to this is that the measurement is made in a region of intrinsically low signal-to-noise ratio. A more serious problem, however, particularly where fluorescence is measured to produce the output pulses, is that fluorescence staining of cells is inherently non-uniform such that two cells of the same size may have different fluorescence intensities, and the result from the fixed threshold pulse width measurement technique depends upon absolute pulse amplitude, as well as on pulse shape. Accordingly, even if two cells have the same size, the bright one will incorrectly be measured as larger. Fluorescence staining is non-uniform due not only to processing variations as a practical matter, but also due to life cycle changes in biological cells which affect the degree of stain absorption.

To circumvent this, Sharpless and Melamed propose a number of amplitude independent estimators for analyzing cytometer pulses to determine particle width. A first evaluation method is a peak width (PW) method wherein total pulse width is measured against a threshold level scaled to some fraction of the pulse height. This result is said to depend only on pulse shape. A second method is a quantile width (QW) method wherein the time required to accumulate some fixed central fraction of the total intensity is recorded by a pair of thresholds scaled to the final value of the integral. Both the peak width (PW) and the quantile width (QW) method require that the pulse shape be stored in a high quality delay line until the peak height or total intensity has been measured and held. A third amplitude independent measurement is the ratio of pulse area to peak height, which is abbreviated "AW".

The approaches described by Sharpless and Melamed generally require the laser beam to be small compared to the cell size. In particular, the effective aperture through which cells or other particles pass is established by means of a slit focused laser beam having a Gaussian intensity distribution, as this is the approximate beam intensity distribution found on most commercially available cytometers. The beam width, and therefore effective aperture, employed ideally is as small as possible, and typically is in the order of or slightly less than the width of the cells being measured. The narrower the beam, the more accurately the pulse shape represents the actual particle shape, and the less it represents the beam intensity distribution. The available beam widths, however, are generally not as narrow as in the Wheeless et al slit-scan systems.

Yet another approach to measuring dimensional characteristics of particles is disclosed in the Curby U.S. Pat. No. 3,919,050. Curby describes a method for analyzing the shape of pulses from either a Coulter Counter or an optical sensor to provide information characterizing the particles producing the pulses. In the Curby method, a secondary pulse producing means is triggered at particular times during the duration of each of the particle pulses to produce secondary voltage pulses whose amplitudes reflect the amplitude of the particle pulse at the time of triggering. These secondary voltage pulses reflect the shape of the primary pulse, and are used to characterize the particles being analyzed.

SUMMARY OF THE INVENTION

Accordingly, it is an object of the invention to provide apparatus and techniques for analyzing pulses from optical devices such as flow cytometers to generate indicators of particle dimensional characteristics, such as size and shape, as well as orientations in a flow stream of non-spherical particles.

It is another object of the invention, to provide such apparatus and methods which do not require the thickness or dimension of the laser beam to be small in the direction of particle travel compared to the size of the cell or other particle which is to be measured.

It is another object of the invention to provide apparatus and methods for rapidly and simply recognizing slight differences among similar cells of a large population.

It is still another object of the invention to provide apparatus and techniques whereby the shape of asymmetrical particles may be determined, and particles of different shape may be differentiated from each other.

It is still another object of the invention to provide apparatus and methods by which the orientation of identical asymmetrical particles in a flow stream may be determined.

In accordance with an important concept of the present invention, it is recognized that the edges of pulses from particle analyzing devices, such as cytometers, contain information concerning particle attributes such as shape, and this information may simply and effectively be ascertained by measuring as characteristic of at least one edge of the pulses on a portion of the pulse edge, which portion is predetermined, such as by empirical measurements, to yield the desired information. While the invention is quite useful in measuring the size of spherical particles, it is also extremely useful in rapidly and simply recognizing slight differences among similar particles of a large group. Where the group of particles is a population of biological cells, the slight differences effectively recognized by employing the present invention have been shown to be sensitive indicators of disease states or of various stages in a normal cellular life cycle.

As one hypothetical situation believed to be useful as an aid to understanding the present invention, an excitation beam may be assumed which has a perfect step function boundary lying in a Y-Z plane. On one side of the boundary beam intensity I is zero, and on the other side intensity I is uniform. (Of course, such a beam would not be found in the real world.) In the hypothetical situation, particles travel at constant velocity v along an X axis perpendicular to the Y-Z plane.

As each particle crosses the beam boundary and enters the beam, a portion of the particle volume is excited (in the case of a fluorescent particle) or a portion of particle surface area illuminated (in the case of a light-scattering particle). For these two respective cases, excited volume may be designated V and excited surface area may be designated S. In either event, V or S, as the case may be, increases with increasing particle displacement along the X axis into the beam. The amplitude of the signal pulse resulting from either fluorescence (from the excited volume V) or light scatter (from the illuminated surface area S) thus represents V or S. Although V and S are functions of particle displacement, with constant particle velocity v they are also functions of time.

In accordance with a more particular concept of the invention, it is recognized that the shape of the particle pulse leading edge reflects the curvature of the portion of the particle which crosses the beam boundary first. More particularly, the shape of the pulse edge is a measure of the rate at which particle optical thickness changes in the Y-Z plane. Expressed alternatively, the shape of the pulse edge is a measure of the rate at which illuminated cross-sectional area changes, where cross sections are defined as being parallel to the beam boundary. As is explained in greater detail in the "Description of the Preferred Embodiments" below, useful information relating to differences in particle sizes, orientations and shapes may be determined, depending on the manner in which the rate of change is interpreted.

As mentioned above, a characteristic of a pulse edge is measured on a predetermined portion of the pulse edge. This is an important feature which permits "tuning" for greatest sensitivity. These are at least two factors which influence what portion of the pulse edge is best from the standpoint of sensitivity. First, for a curved surface entering the beam, the rate of change of excited volume V or illuminated surface area S is greatest as the particle just enters the beam. Second, for "real world" beam intensity distributions, there are regions within the beam where beam intensity I varies rapidly with position, and pulse edge portions resulting from particle interaction with the beam in these regions is not a sensitive indicator of particle characteristics. These pulse edge portions may be avoided, and pulse edge portions resulting from particle interaction with other regions within the beam, where beam intensity I varies gradually with position, may be analyzed.

In accordance with another important concept of the invention, it is recognized that the present invention may be employed even where the beam intensity distribution is other than a step function, for example having a Gaussian intensity distribution.

For measuring a characteristic of at least one edge of the pulse on a predetermined portion of the pulse edge, a number of approaches might be employed. Two possible examples are taking the derivative of the pulse edge on a particular portion, and applying the pulse to a Fast Fourier Transform analyzer. However, a particularly advantageous technique is to measure pulse edge width between a lower and an upper threshold value, which preferably are established as constant fractions of the peak amplitude of the particular pulse. This may also be viewed as normalizing the pulses where peak amplitude is used as a reference. As a further illustration that there are a number of ways in which a particle edge characteristic may be determined, it will be appreciated that a pulse edge width measurement between fixed amplitude thresholds is the reciprocal of slope, and therefore has the same information. This same information may also be expressed in terms of a differential.

While threshold establishment as a fixed fraction of pulse amplitude is generally known in the prior art, for example in the peak width (PW) cell sizing method, as a means for circumventing problems caused by non-uniform fluorescence staining, the constant fraction threshold has further advantages in the context of the present invention. For example, and as explained in greater detail below in the context of sizing spheres, establishing the threshold as constant fractions of peak amplitude is quite important in the results obtained, quite apart from problems caused by non-uniform fluorescence staining. Moreover, the constant fraction or normalizing approach is an important feature when the beam intensity distribution is non-uniform, particularly Gaussian.

Briefly stated, and in accordance with a particular aspect of the invention, there is provided an analyzer adapted for connection to an output of a device, such as a flow cytometer, of the type which conveys a particle, such as a cell, through a beam of electromagnetic radiation and which responds to radiation resulting from interaction of the particle with the beam to output a resultant signal in the form of an electrical pulse as the particle enters and passes through the beam. The radiation resulting from interaction of the particle with the beam may, for example, be scattered light or secondary fluorescence. Specifically, the analyzer serves to determine an attribute of the particle and includes means for measuring a characteristic of at least one edge of the pulse on a predetermined portion of the pulse edge as an indication of the particle characteristic. As a particular example, the pulse edge characteristic which is measured may be the width of at least one edge of the pulse between two threshold values. Preferably, the analyzer includes means for establishing the two thresholds at constant fractions of the peak amplitude of the pulse.

In the case where the one edge of the pulse is the leading edge, the analyzer thus measures pulse rise time. This rise time measurement has been found to have increased resolution compared to the previously-described time-of-flight methods because only that portion of a pulse in which the cell or particle predominates in changing the signal is measured.

Particle characteristic information so determined for a population of cells can, in accordance with another aspect of the invention, be analyzed, for example through distribution analysis techniques, to reveal subtle differences between cells. The shape of a distribution function can be compared to an empirically-determined data base to recognize disease states, or particular cellular life cycle stages.

As one example relating to cell shape and orientation, if a population of substantially identical prolate ellipsoid (oblong) cells are passed through a flow cytometer and the output pulses analyzed by plotting a distribution of pulse edge rise times between two thresholds established at constant fractions of the peak amplitudes of the respective pulses, then a distribution having one or more peak is observed. Each individual constant fraction pulse rise time depends upon the curvatuure of the particle portion which enters the beam first. Each peak in the distribution representation represents a particle orientation which is preferred to at least some extent, as a matter of fluid dynamics, by particles in a flow stream. The magnitudes of the distribution peaks, the relative rise times which they represent, and their spacing can all be examined to yield useful information about the cells. Information can be inferred concerning the relative curvatures of various portions of the cells, as well as degree of deviation from a perfect spherical shape.

As another example, for a population of spherical particles of different sizes, the distribution reveals the range of sizes involved.

The aspect of the invention where only a predetermined portion of the pulse edge is selected for producing the indication of particle characteristics is particularly beneficial in the case of a beam edge having a Gaussian intensity distribution because the thresholds between which pulse rise time is measured may readily be established so that measurement is accomplished in a region of the beam where its intensity changes relatively slowly with position. A further advantage is that beam width may be much greater than the width of the particle or feature to be measured.

Briefly stated, and in accordance with another aspect of the invention, apparatus for determining an attribute of a particle includes means for conveying the particle through a beam of electromagnetic radiation, and means responsive to radiation resulting from interaction of the particle with the beam to output a resultant signal in the form of a pulse as a particle enters and passes through the beam. The apparatus further includes means for measuring a characteristic of at least one edge of the pulse on a predetermined portion of the pulse edge, for example pulse edge width between two threshold values. Preferably, the apparatus include means for establishing the two thresholds at constant fractions of the peak amplitude of the pulse.

In accordance with still another aspect of the invention, apparatus is provided which may be employed for obtaining orientation information for identical asymmetrically shaped particles which are conveyed along a flow axis through a beam of electromagnetic radiation. In accordance with this aspect, the apparatus includes means responsive to radiation resulting from interaction of the particle with the beam to generate a signal in the form of a pulse as a particle enters and passes through the beam. The apparatus includes first measurement means for measuring a characteristic of at least one edge of the pulse on a predetermined portion of the pulse edge as an indicator of the curvature of the portion of the particle which is first entering or last exiting the beam, depending upon whether the one edge of the pulse is the leading or the trailing edge. The apparatus includes second measurement means for independently measuring another characteristic of the pulse to obtain an independent indication of particle size. Lastly, means responsive to the pulse edge characteristic measurement and the other characteristic measurement correlates the measurements to yield orientation information. As one particular example of the other characteristic measured by the second measurement means, the second measurement means may employ one of the time-of-flight measurements, such as the peak width (PW) method referred to above.

In accordance with another aspect of the invention, a method for analyzing the output pulse from a device of the type which conveys a particle through a beam of electromagnetic radiation and which responds to radiation resulting from interaction of the particle with the beam to output a resultant signal in the form of a pulse as the particle enters and passes through the beam includes the steps of measuring a characteristic of at least one edge of the pulse on a predetermined portion of the edge as an indication of a particle attribute.

It should be noted that aspects of the present invention have been disclosed in literature published less than one year prior to the filling date hereof. Specifically: J. F. Leary, P. Todd, J. C. S. Wood, and J. H. Jett, "Laser Flow Cytometric Light Scatter and Fluorescence Pulse Width and Pulse Rise-Time Sizing of Mammalian Cells", *J. Histochem. Cytochem.*, Vol. 27, No. 1, pp. 315–320 (1979), the entire disclosure of which is hereby expressly incorporated by reference herein. This identification of a specific publication should not, however, be taken as implying that other acts of publication less than one year prior to the filing date hereof have not occurred, and no such representation is made or intended herein.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENTS

Figure 1:
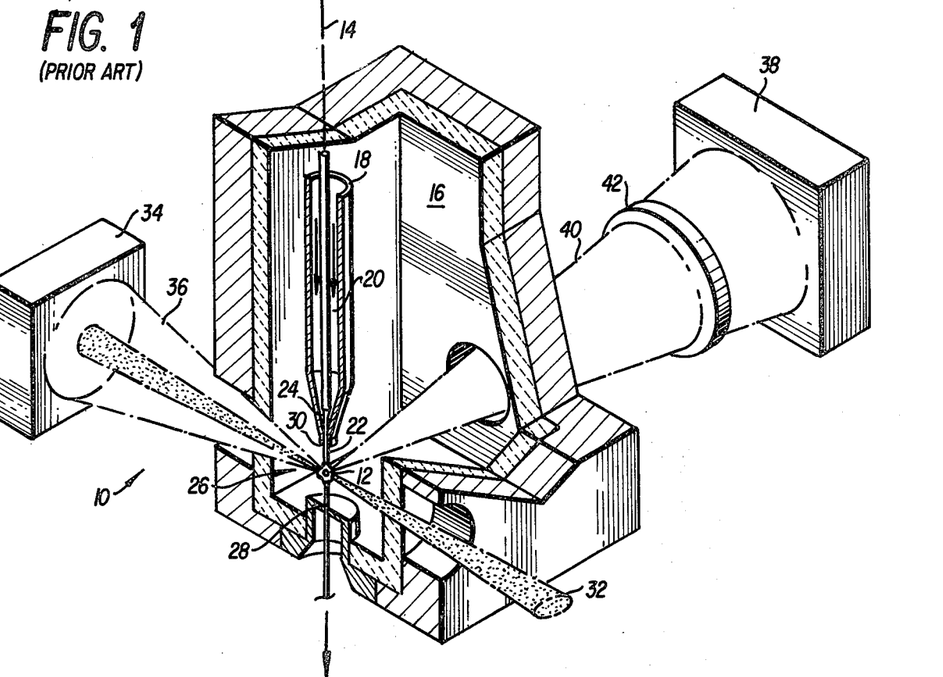
FIG. 1 is an isometric view of a prior art flow cytometer flow chamber with a portion thereof cut away.

Referring first to FIG. 1, the flow and sensing portion 10 of a prior art flow cytometer is illustrated in highly schematic form. For conveying cells, such as the greatly enlarged exemplary cell 12, along a flow axis 14, a flow chamber 16 employing a sheath flow geometry is employed. Cells in suspension enter the chamber 16 via an axial specimen tube 18 and are enveloped in a coaxial sheath of water 20. A stream 22 of cells in suspension exits the specimen tube 18 and is constricted in a flow nozzle 24. At this point, the cell stream 22 has a diameter approximately that of the individual cells, such as the cell 12.

The cell stream 22 flows across a gap region 26 and exits the chamber 16 via an exit aperture 28. The gap region 26 is typically 200–350 micrometers from the exit 30 of the flow nozzle 24 to the entrance of the exit aperture 28, with a typical flow rate of 10–50 cm/sec. The flow is laminar.

A beam 32 of electromagnetic radiation is generated, for example, by a 0.1–0.5 watt, 488 nanometer argon-ion laser (not shown), and focused to a generally elliptical cross-section beam, typically having a Gaussian intensity distribution in the direction of flow. The laser beam 32 is directed toward the flow axis 14 such that particles carried by the flow stream 22 pass through the beam 32, ideally one-by-one. In various known devices of this type, different particular configurations of the beam 32 are employed. The beam width in the direction of flow may be either relatively wide or relatively narrow compared to the cell or other particle dimension, and the beam 32 cross-section may be circular, as well as ellipitical. Typically, the intensity distribution is Gaussian, as this is a characteristic of laser illumination. However, such devices are not limited to laser illumination. On particular example of another source of electromagnetic radiation is a mercury lamp. Similarly, the beam intensity distribution need not be Gaussian.

The apparatus of FIG. 1 additionally includes a pair of representative means responsive to radiation resulting from interaction of particles, such as the representative cell 12, with the beam 32 to output a resultant radiation intensity signal in the form of a pulse as the particle enters and passes through the beam 32. One particular such radiation responsive means is a photodetector 34 so positioned that it is responsive to small angle light scatter, such as is represented by the beam 36. Thus, the resultant radiation to which the photodetector 34 responds specifically results from interaction of particles with the beam 32 to produce scattered light. While the positioning of the particular photodetector 34 is such that it responds to small angle light scatter, it will be appreciated that numerous orientations are employed in the art for any desired light scatter angle. The other exemplary means responsive to radiation resulting from interaction of particle with the beam 32 is a photodetector 38 which is so arranged to respond to secondary fluorescence resulting from interaction of particles with the beam 32. The secondary fluorescence light is represented by the beam 40. In order that the photodetector 38 may respond to secondary fluorescence, and not to illumination from the excitation beam 32, it is provided with a suitable wavelength filter 42 which passes the wavelength of desired secondary fluorescence, and blocks wavelengths of the excitation radiation beam 32.

It will be appreciated that the representation of FIG. 1 is highly schematic and is intended only to illustrate the concepts of the present invention in the context of actual devices. Five particular examples of commercially available flow cytometers constructed generally in accordance with the principles illustrated in FIG. 1, and to which the present invention has been applied, both as an output analyzer and in combination to produce a new device, are the Ortho Instruments (Westwood, Mass.) Cytograf Model 6300, and Cytofluorograf Model 4802A; the Becton-Dickinson (Mountain View, Calif.) FACS II; and the Coulter Electronics (Hiealeah, Fla.) TPS-1 and TPS-2 fluorocytometers.

Figure 2:
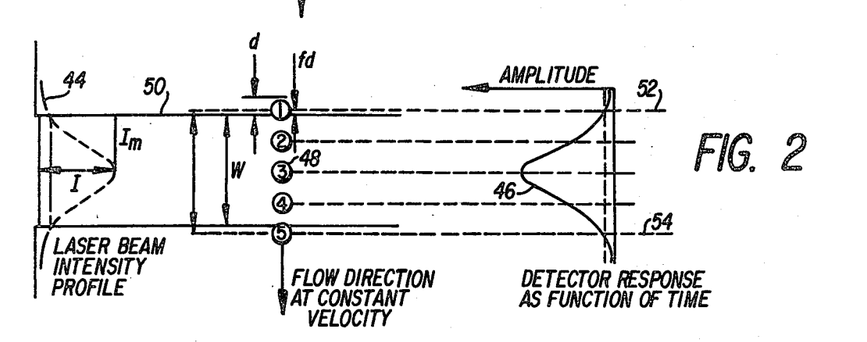
FIG. 2 is a representation of the excitation laser beam intensity profile (in the direction of particle travel) in the apparatus of FIG. 1, with five different positions of a particle passing through the beam specifically identified, together with a curve showing the shape of the output pulse.

Referring now to FIG. 2, there is shown a composite diagram illustrating a typical laser beam intensity profile 44 such as might be found for the beam 32 in the apparatus of FIG. 1 in the direction of flow (downward along the axis 14). The profile 44 is Gaussian as is typical in such systems, intensity being designated I, and maximum intensity designated $I_m$. Effective beam width W is defined between the $1/e^2 \times I_m$ intensity points on the beam profile 44.

Near the right-hand side of FIG. 2 is a detector response profile 46, which may be either scattered light intensity or fluorescence intensity depending upon the particular apparatus. The detector response curve is shown as a function of the time a particle spends passing through the beam.

In FIG. 2, a representative particle 48 is depicted at five different points, identified as 1, 2, 3, 4 and 5, on its path along the flow axis 14 depicted in FIG. 1. In the particular example chosen for FIG. 2, it will be seen that the beam width W is much greater than the diameter of the exemplary particle 48. As will now be demonstrated, this situation results in a relatively lower resolution with previously known time-of-flight cell sizing methods, but in higher resolution with the present pulse rise time system. With the present pulse rise time system, results are obtained which would require a smaller beam width in other systems. Thus, it can be said that the present system makes the effective beam width smaller than the effective beam width would be for the same beam in a time-of-flight system.

More particularly, in FIG. 2 a dimension d representative of cell diameter is shown at the upper edge 50 of the beam. Cell diameter as measured by time-of-flight sizing methods depends upon the choice of thresholds 52 and 54 which determine what fraction f of the actual cell diameter d is measured, and on the laser beam width W. In fixed threshold time-of-flight systems which are amplitude independent, f is an unknown and varying fraction of the cell diameter. However, in amplitude independent pulse width approaches (such as prior art peak width) and in pulse rise time sizing approaches of the present invention, f is a known constant fraction of the cell diameter d.

In the prior art peak width (PW) method, the width of the pulse represented by the response curve 46 is equal to the expression $W + 2fd$. Since the pulse 46 width depends upon the beam width W, and is independent of particle size d, it will be apparent that in prior art time-of-flight sizing methods, resolution decreases with large laser beam widths W and increases with smaller beam widths W.

In accordance with an important concept of the present invention, previously unutilized information in the pulse response curve 46 is employed. Specifically, rather than measuring pulse width between the thresholds 52 and 54 across the entire detector output pulse 46, a characteristic of the rising or falling portion (edge) only thereof, and on a predetermined portion of the edge, is measured. It is especially important where Gaussian beam edge intensity distributions are involved that a predetermined portion of the pulse edge be selected, in which predetermined portion changes in pulse amplitude are the result of changes in illuminated cell volume (or surface area) and not a result of beam intensity changes. In particular embodiments, pulse edge width is measured between two threshold values which preferably are established at constant fractions of the peak amplitude of the pulse. Thus, a pulse rise time or fall time is measured, depending on whether the leading or trailing edge of the pulse is examined. It has been discovered that resolution is greatly improved, even where Gaussian beam intensity distributions are present, when these two thresholds are established at relatively low amplitudes.

More specifically, it is believed that particle curvature information is present in the leading edge of the pulse represented by the detector response curve 46. Specifically, the leading edge of the response curve 46 is a function of the curvature of the portion of the particle which interacts first with the beam 32 edge. Similarly, the trailing edge of the pulse 46 contains information concerning the radius or curvature of the portion of the particle last exiting the excitation beam 32.

In the fluorescence situation where an excited volume of the particle emits fluorescence light, and the particle is relatively transparent such that fluorescence is not reabsorbed, fluorescence, such as measured by the photodetector 38 of FIG. 1, is proportional to beam intensity I times that particle volume V which is excited or illuminated by the beam. The signal pulse as represented by the curve 46 is therefore a product of intensity I times illuminated volume V as a function of time. The particle volume V which is excited is not at all times the entire volume of the particle, but rather depends upon the degree to which the particle is projecting into the beam 32 and is thereby illuminated.

A similar result is obtained for light scatter, particularly in the near forward direction (small angle). Specifically, light scatter in the near forward direction is proportional to intensity I times particle illuminated or swept onto surface area S. The signal pulse is therefore a product of intensity I times swept out surface area S as a function of time. This also applies to particles which are fluorescent on the surface only.

In this description of what is believed to be the correct explanation of the operation of the invention, it is a premise that, for a particle having a curved surface entering the beam 32, volume V or surface area S, depending upon whether the particular detector responds to fluorescence or light scatter, intensity increases at an initial rate which depends on the curvature of the particle portion which enters the beam first. For spherical particles, where thresholds are established as constant fractions of intensity, it takes longer for a larger particle than a smaller particle to penetrate the beam beginning from the point where the first (lower) threshold is crossed (just above the noise) up to the point where the second threshold is reached. A similar statment may be made for particles exiting the beam, in which case the first threshold crossed is the upper one, and the second threshold crossed is the lower one. Thus, pulse edge width directly indicates sphere size. If a population of spherical particles are passed through the beam and the constant fraction pulse edge widths recorded, the resultant edge width data are sensitive indicators of sphere size.

For identical size and shape oblong particles passed through the beam, constant fraction pulse edge width indicates orientation. For oblong particles entering end-on, pulse rise time is slower and pulse edge width greater than for oblong particles entering sideways.

From the above, it will be appreciated that the particular particle attribute which the present invention differentiates between similar cells of a population depends upon the shape of the cells. The most straightforward example is sizing of spherical cells, for example lymphocytes. Another useful example is determining orientation of prolate ellipsoid cells, for example mammalian tissue culture cells. These are, however, cell shapes for which results are poor. One example is squamous cells which are flat and relatively rectangular. If such a cell enters the beam edge-on, the illuminated optical thickness (or cross-sectional area) changes abrubtly as the cell first enters, reflecting the sharp curvature of the corners, but the rate of charge thereafter mainly reflects cell extent perpendicular to the direction of travel and velocity, and not shape.

The particular thresholds, and thus the particular pulse edge portion which is measured, preferably are selected expirically for greatest sensitivity, or, expressed alternatively, maximum measured difference between different particles. As a general guideline, relatively lower threshold ranges produce greatest sensistivity. However, if thresholds are too low, signal-to-noise ratio is unacceptable. As one particular example for the two thresholds, which is in no way intended to limit the scope of the invention is its broader aspects, 5% and 35% of the peak amplitude have been employed experimentally for the two thresholds. As another particular example, 3% and 10% thresholds have been employed. This is much more sensitive, but noise is more of a problem. From these particular examples and from the description of the measurement itself, it will be apparent that the pulse edge measurement of the present invention contrasts sharply with the traditional use of 10% and 90% of peak amplitude for electrical pulse rise time analysis in many fields.

In accordance with the invention, it is recognized that for a Gaussian beam intensity distribution, the most accurate results are obtained when the thresholds are set relatively low, in the order of less than one-third of the peak amplitude, such that the particle parameter, either V or S, is changing faster than the beam intensity as a function of position, which is converted to a function of time by virtue of particle motion at an assumed constant velocity. In particular, for a Gaussian intensity distribution as represented by the curve 44, the rate of change along the beam as a function of distance (and therefore time as the particle moves into the beam) is less near the edges than at most other points. (An exception is the peak of the Gaussian distribution curve, where intensity is rather constant, but falls off rapidly on either side making the region near the peak difficult to use in practice). Thus the threshold approach of the present invention allows a measuring region to be selected where beam intensity changes slowly.

More particularly, near the beam edges, beam intensity I can be assumed to be slowly changing with respect to distance. Change in the output pulse amplitude as represented by the detector response curve 46 depends primarily on the change in illuminated volume V (or illuminated surface area S in the case of light scatter). Therefore, the rise time of the pulse 46 between constant fractions of peak amplitude is a measure of the rate of change of volume, which reflects size or shape as represented by the curvature of the particle portion involved.

At other points in the travel of the particle 48 through the beam, such as between positions 2 and 4, beam intensity I varies rapidly with position. The rate of change in beam intensity as the particle moves through these regions is much greater than the rate of change of illuminated volume V (or surface area S), and therefore far less information concerning particle curvature is contained in corresponding regions of the detector response curve 46.

In the operation of the invention as described above, the ideal beam intensity distribution profile would be a step function, that is, having a very sharply defined edge at which intensity goes from zero to a fixed value, and then remains at the fixed value throughout the beam. However, in presently available instruments, employing laser excitation, such beam intensity profiles are generally not found. Surprisingly, we have discovered that the beam edge intensity distributions which do result in presently available laser beams can be effectively utilized for obtaining particle information.

Figure 3:
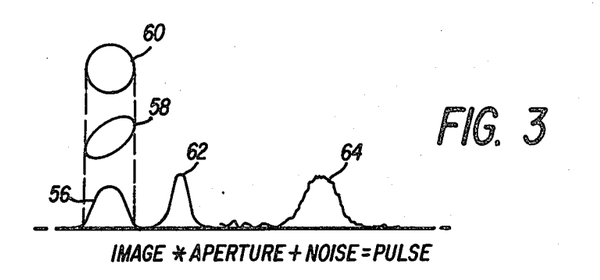
FIG. 3 is a representation, taken from the Sharpless annd Melamed article referred to above, of the output pulse resulting from the convolution integral of a cellular image and an effective aperture having a width slightly less than the dimension of the cell in the direction of flow.

Another beam characteristic is depicted in FIG. 3, which is similar to a figure in the Sharpless and Melamed article entitled "Estimation of Cell Size From Pulse Shape In Flow Cytofluorometry", which is referred to above. FIG. 3 illustrates another form of beam 32, a relatively narrow beam, which has a dimension in the direction of particle travel in the order of or less than the dimension of the particle in the direction of travel. This is in contrast to the situation depicted in FIG. 2 wherein the beam 32 is relatively wide having a dimension in the direction of particle travel larger than the dimension of the particle in the direction of travel. It is a feature of the present invention that accurate results may be obtained with either type of beam.

While reference may be had to the Sharpless and Melamed article for a more detailed description of FIG. 3 herein, in FIG. 3 a truncated parabola 56 represents the approximate projection into one dimension of the intensity distribution of an ellipsoidal distribution 58 or spherical distribution 60. This illustration indicates that particle width as measured by time-of-flight circuits represents extent in one direction only, i.e., the direction of flow. In accordance with an important aspect of the present invention, it is recognized that the shape of the curve for the projection of the representative spherical distribution 60 is actually not identical to the curve for the projection of the representative ellipsoidal distribution 58. In particular, the shapes of the rising and falling portions of the projection 56 are established by relative particle thickness as a function of distance along the particle (thicknesses in successive planar cross sections perpendicular to the direction of particle travel).

The curve 62 of FIG. 3 represents the effective aperture function, which, in most instruments, is approximately equivalent to the intensity profile of the illuminating beam 32 along the direction of particle motion. The resultant fluorescence pulse 64 has a shape which is the convolution of the image 56 and aperture 62 (both functions of position), and whose time t scale is related to the scale of distance in the x (flow) direction by $t = x/v$, where v is particle velocity. The electrical pulse which is finally measured represents this fluorescence pulse 64, mixed with noise and perhaps modified by the dynamic characteristics of the detector in amplifiers.

From the discussion above concerning the difference in the shapes of the rising and falling portions of the FIG. 3 projection 56, depending on relative particle thicknesses as a function of distance along the particle, it will be appreciated the rise and fall rates of particle pulses such as the pulse 64 reflect this same information. The pulse 64 rise and fall rates are in fact a function of particle thickness. In previous time-of-flight particle sizing approaches, these rise and fall rates did in fact influence overall pulse duration measurement (established by above-threshold pulse duration), but this influence was unrecognized. Stated differently, prior art time-of-flight particle dimension measurements, while normally considered to measure particle extent only in the direction of travel, are influenced by cell thickness in directions perpendicular to the direction of travel. In accordance with the present invention, this information is recognized and utilized.

Figures 4, 8:
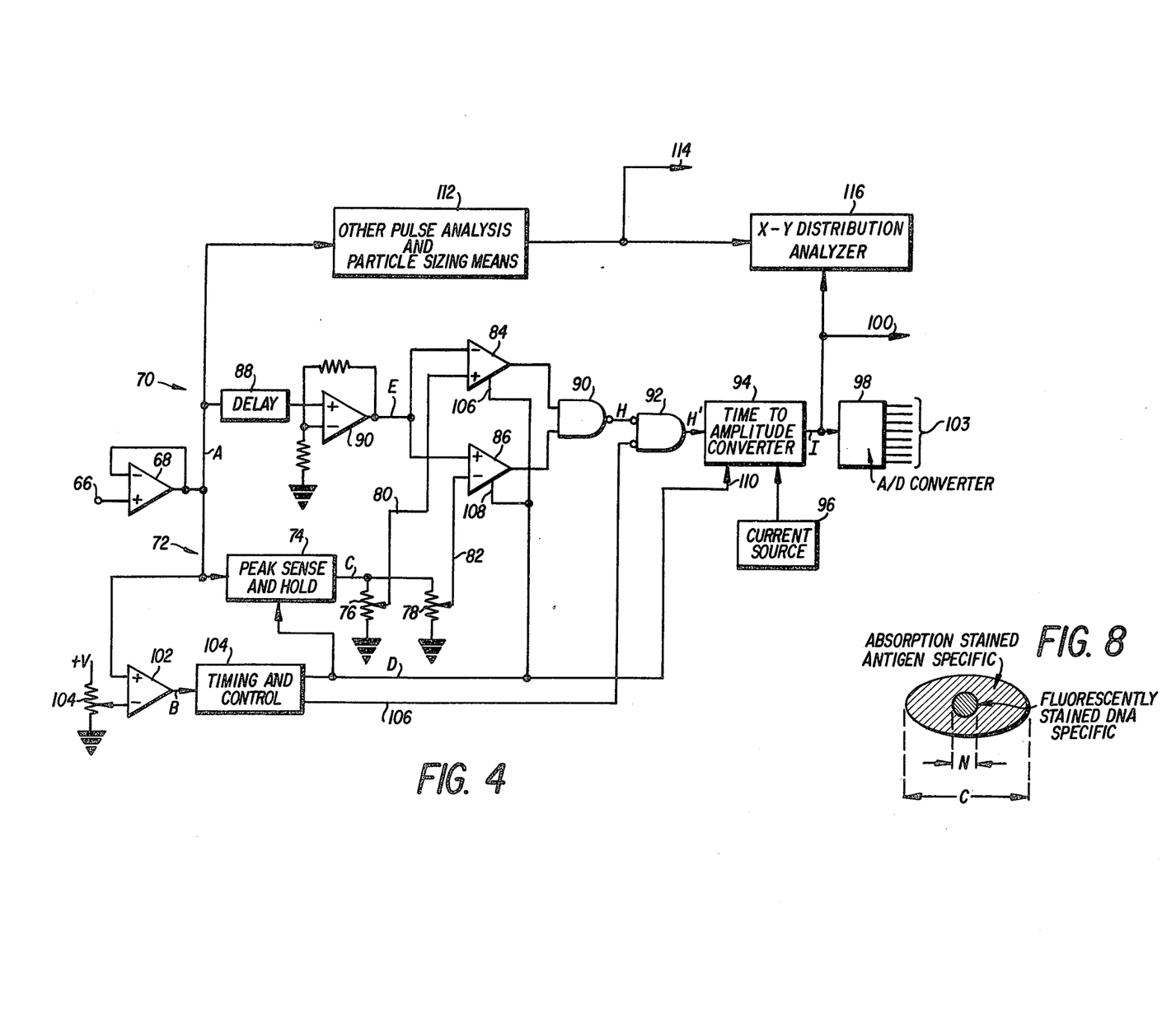
FIG. 4 is a diagram of an exemplary electrical circuit for implementing the pulse rise time analysis technique of the present invention.
FIG. 8 is a diagram depicting selective staining of biological cell as a step in a method for obtaining nuclear to cytoplasmic (N/C) diameter ratio.

Referring now to FIG. 4, there is illustrated an electrical schematic diagram of one form of circuit suitable for making pulse rise time measurements between constant fractions of the peak amplitude of an incoming pulse. As stated above this particular pulse measurement technique is convenient for measuring a characteristic of at least one edge of a particle pulse on a predetermined portion of the pulse edge, although other approaches such as taking the derivative of selected portions of the pulse edge or applying the pulse edge to a Fast Fourier transform machine are also potentially useful. The specific circuit shown in FIG. 4 forms no part of the present invention, but rather was designed and built by Robert Habbersett, and extensively tested by Richard Hiebert.

In FIG. 4, an input pulse is introduced at a terminal 66 and passed through a unity gain buffer amplifier 68 which drives an input pulse line A. For the basic measurement required by the invention, the pulse on the input pulse line A is applied to two channels 70 and 72 such that a copy of the original pulse can be compared at a later time with constant fractions of itself. In the lower channel 72, the input pulse line A is applied to a peak sense and hold circuit 74 which supplies a stored peak pulse amplitude line C connected to the upper ends of two threshold adjusting potentiometers 76 and 78. The settings of the potentiometers 76 and 78 serve to establish respective upper and lower threshold voltage levels on reference lines 80 and 82. The upper threshold reference line 80 is applied to the non-inverting (+) input of an upper threshold comparator 84, and the lower threshold reference line 82 is applied to the inverting (−) input of a lower threshold comparator 86.

In the upper channel 70, the input pulse line A is applied to the input of an eight microsecond delay line 88, which may be a high fidelity delay line manufactured by Allen Avionics Electronics, Inc., Mineola, NY. The output of the delay line 88 is connected through an amplitude restorer amplifier 90, driving a delayed, restored input pulse line E, which is applied to the signal inputs of the two comparators 84 and 86, which signal inputs are respectively the inverting (−) input of the comparator 84 and the non-inverting (+) input of the comparator 86.

The outputs of the comparators 84 and 86 (lines G and F) are applied to the inputs of a NAND gate 90, having an output designated H connected to one input of a low activated AND gate 92 (functionally equivalent to a conventional NOR gate) having an output designated H'. H' is high during the time the delayed, restored pulse signal E is between the two thresholds.

Finally, the line H' is connected to the input of a time-to-amplitude converter 94 which linearly charges an internal capacitor (not shown) from a current source 96 while the low activated AND gate 92 is active and H' is high. An output line I of the time-to-amplitude converter 94 is connected to the input of an analog-to-digital converter 98, as well as to an external output point 100.

To control the operation of the circuit of FIG. 4, the pulse input line A is connected to the non-inverting (+) input of a trigger comparator 102, which has its inverting (−) input connected as a reference input to a variable potentiometer 104. A comparator 102 output line B is connected to suitable timing and control logic 104 which, when triggered by line B going high, outputs a control pulse on line D, which remains high for approximately seventy microseconds. The timing and control logic 104 also serves to output an enabling signal on a line 106 which is connected to the lower input of the low activated AND gate 92 for the purpose of allowing the low activated AND gate 92 to pass the pulse width signal for the leading edge of an input pulse, but block the pulse width signal for the trailing edge of the input pulse. The control pulse line D is also connected to respective enabling inputs 106 and 108 of the threshold comparators 84 and 86, as well as to an enabling input 110 of the time-to-amplitude converter 94.

Additionally illustrated in FIG. 4, is a means 112 for measuring another characteristic of the input pulse, independently of the pulse rise time measurement effected by the portions of the FIG. 4 already described, to obtain an independent indication of particle size. This other pulse analysis and particle sizing means 112 may implement any of the previously known cell sizing methods, but preferably comprises amplitude independent peak width (PW) cell sizing apparatus. For convenience, the measurement means generally comprising the two channels 70 and 72 for measuring the width of an edge of a voltage pulse between two fractions of its peak amplitude may be designated a first measurement means, and the other pulse analysis and particle sizing means 112 may be termed a second measurement means. The output of the other pulse analysis and particle sizing means 112 is shown connected to a terminal 114.

The remaining element in FIG. 4 is a means, specifically an X-Y distribution analyzer 116, which is responsive to the pulse rise time measurement output of the time-to-amplitude converter 94 and to the other measurement from the means 112. The X-Y distribution analyzer 16 serves to correlate these two measurements.

For convenient connection to other circuitry, such as a computerized analysis system, output lines 118 of the analog to digital converter 98, as well as the outputs 100 and 114 are provided.

Figure 5:
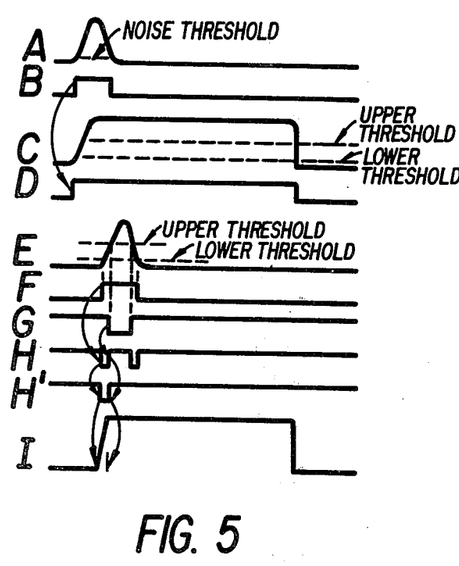
FIG. 5 depicts waveforms occurring during the operation of the circuit of FIG. 4 as a single particle passes through the apparatus of FIG. 1.

The operation of the circuit of FIG. 4 will be better understood with reference to the waveforms of FIG. 5 having letter designators corresponding to identically designated lines in FIG. 4. When amplitude of the input pulse A exceeds the threshold established by the potentiometer 104, the trigger comparator 102 is actuated and B goes high. When B goes high, the D output line of the timing and control logic goes high, enabling the peak sense and hold circuit 74. The output C thereof follows the input pulse signal A and holds the peak value (until D goes low seventy microseconds later). The analog value on stored peak pulse amplitude line C is applied to potentiometers 76 and 78 which are manually set to provide respective upper and lower threshold voltages as represented by the dash lines shown superimposed over the waveform C of FIG. 5.

A sufficient time later, as established by the delay line 88, the restorer amplifier 90 output line E outputs a delayed replica of the input pulse on the line A. This delayed replica is applied to the comparators 84 and 86 (both comparators 84 and 86 being enabled by the control pulse line D being high).

Initially, the voltage on the non-inverting (+) input of the lower threshold comparator 86 is less than the reference voltage applied to its inverting (−) input, and the output F thereof is therefore high. Conversely, the voltage applied to the inverting (−) input of the upper threshold comparator 84 is less than the reference voltage applied to its non-inverting (+) input, and the G output thereof is high. With G high and F low, the NAND gate 90 is not active, and its output H is high. The delayed replica pulse on line E is applied to the comparators 84 and 86. When the lower threshold voltage is reached as established by the potentiometer 78 as a fixed fraction of the peak magnitude, the lower comparator 86 output F goes high, activating the NAND gate 90, so that the output H thereof goes low. When the upper threhold is established by the potentiometer 76 is reached, the output G of the upper comparator 84 goes low, and the NAND gate 90 is again inactive.

While in accordance with the invention the widths of the leading or trailing edges, or both, of the input pulse may be examined, in this particular embodiment only the width of the leading edge is examined. Therefore, the low activated AND gate 92 is employed as a gate, and a suitable timed control input on the line 106 from the timing and control logic 104 enables the low activated AND gate 92 to pass the signal on the line H to the output H' thereof only on the leading edge of the input pulse.

The width of the pulse H' is converted to an analog voltage in the time-to-amplitude converter, as indicated by the waveform I. The line I is the basic output resulting from the pulse rise time measurement concept of the invention, and may be employed in various manners as described elsewhere herein.

Figure 6:
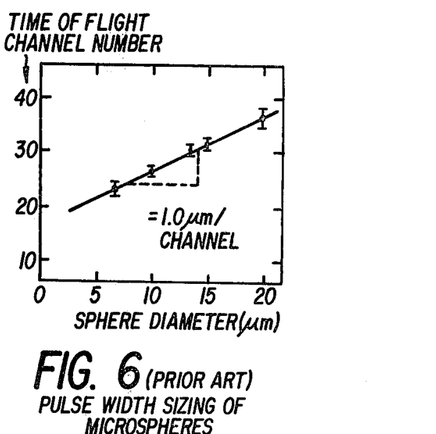
FIG. 6 is a curve showing the resolution of a prior art time-of-flight particle sizing system.
Figures 7, 9:
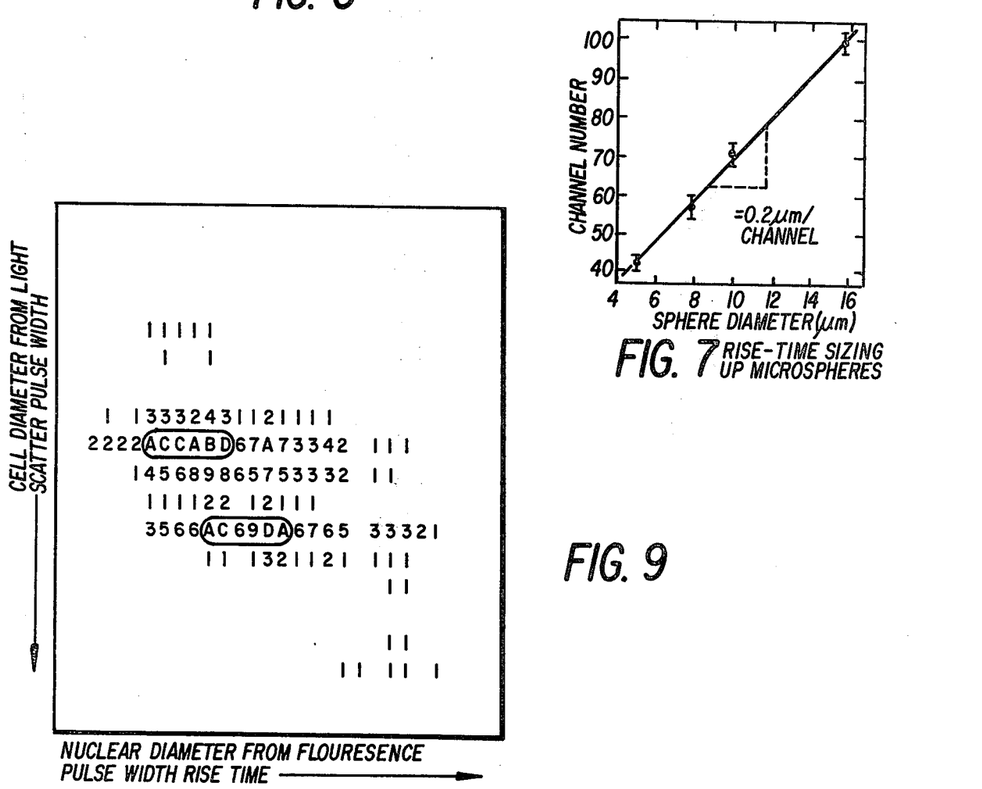
FIG. 7 is a curve showing resolution of a pulse rise time measurement system in accordance with the present invention.
FIG. 9 is the graphical result of a two parameter distribution analysis illustrating results which may be obtained by apparatus according to the present invention.

Referring now to FIGS. 6 and 7, the relative resolution of a prior art time-of-flight (T.O.F.) particle sizing technique and the pulse rise time sizing technique to the invention are compared. Specifically, FIG. 6 is a sphere diameter calibration curve for apparatus employing the prior art amplitude independent peak width (PW) method, with pulse widths measured from a 5% peak amplitude threshold on the rising side of the signal to 5% of the peak amplitude threshold on the trailing edge of the signal. Light scatter pulse width sizing of the microspheres was employed, using an Ortho Instrument Cytofluorograph Model 4802A. Similar resolution has been achieved on the Becton-Dickinson FACS II. It can be seen that while the dynamic range is rather wide, resolution is low, the slope of the line being approximately 1.0 micrometer per channel.

FIG. 7 shows microsphere calibration results for apparatus employing pulse rise time sizing in accordance with the present invention. To obtain the curve of FIG. 7, light scatter pulse rise time sizing between 10% and 35% of peak amplitude thresholds on the rising side of the signal were made, the measurements being made on the Becton-Dickinson FACS II. Similar resolution has been achieved on the Ortho Instruments Cytofluorograph Model 4802A. Comparing FIGS. 6 and 7, it can be seen that the techniques of the present invention have approximately five times the resolution of the particular prior art technique used as a basis for comparison.

The sensitivity of apparatus embodying the invention to the curvature of particle portions interacting first with the beam may be put to a number of advantageous uses. For determining particle shape, assuming a population of substantially identical asymmetrical cells, a representative sampling of cells may be run through a cytometer, individual pulse rise time measurements made, and the distribution results plotted in the form of a histogram. For asymmetrical particles, a number of particular peaks may be found on the histogram, with other measurements falling between peaks. In accordance with the invention, this distribution has now been recognized as representing various preferred orientations of particles carried in a laminar flow stream. Such particles tend to align in stable flow with the long dimension of the particles in the direction of flow, and this orientation generally produces the largest peak on the histogram, with the peak indicating the particular curvature of the end of the particles. However, in such flow systems, other semi-stable orientations exist, and these result in other peaks on the histogram, corresponding to the particular curvatures of the portion of the particle which enters the beam first in these particular orientations. Accordingly, an analysis of such a histogram yields information concerning particular curvatures found at various points on the particles. In summary, since particles tend to orient in many directions a composite pulse rise time measurement pattern yields information about the overall shape of the particles. Each peak in the distribution corresponds to a particular particle orientation, with the position of the peak indicating the curvature of the portion of the particle crossing the laser beam first.

Further, when pulse rise time measurements are correlated with another measurement, for example pulse width, such as would be output by the means 112 of FIG. 4, orientation of a single asymmetrical particle may be determined. If the overall size and shape of the particle is known, correlating particle length in the direction of flow as determined by the peak width (PW) method with the curvature information from the present rise time method allows the orientation to be determined. This is similarly useful in detecting particle doublets and clumps.

As another example, light scatter pulse edge measurements of the present invention are useful in discriminating between live and dead cells. In particular, it has been found that dead cells scatter less light than live cells of the same size. By analyzing a single particle pulse, cell diameter can be accurately and with high resolution determined from pulse rise time between constant fractions of peak amplitude, while at the same time peak amplitude alone indicates light scatter magnitude. The two measurements can be immediately correlated and compared with a data base to determine whether the cell is alive or dead. It will be appreciated that since the pulse rise time measurement to determine cell diameter is made between constant fractions of peak amplitude, the diameter determination is accurate regardless of the amplitude of the light scatter intensity.

Other uses include accurate sizing of light scatter and fluorescence particle standards of known size to be used both for accurate sizing of particles of unknown size and for determination of the proper functioning of the basic flow cytometer. Additionally, if particle size is known, these measurements can yield information concerning the velocity of the fluid in which the particle is traveling.

As an example of one particular use of the techniques of the present invention, cytoplasmic to nuclear diameter (N/C) ratio can be measured with paired pulse rise time and pulse width circuits, and a two parameter distribution analyzer such as the X-Y distribution analyzer 116 of FIG. 4. As depicted in FIG. 8, the cell nuclei are stained with a DNA specific fluorescent stain, such as acriflavine. The cell cytoplasm is stained either immunoenzymatically or by another histochemical staining method, with a light absorbing stain. When cells such as are depicted in FIG. 8 pass through the cytometer, in the preferred orientation with the cell longer dimension extending in a direction of flow, light scatter measurements, such as from the other pulse analysis and particle sizing means 112 of FIG. 4, determine the overall linear dimension of the cell involved. At the same time, fluorescence pulse rise time measurements determine the radius, and therefore the diameter, of the nucleus. It will be appreciated that since the constant fractions for the pulse rise time measurements are established as a fixed fraction of peak nuclear fluorescence, the accuracy of the nuclear size measurement is unaffected by either variations in fluorescent stain intensity or by the presence of the light absorbing stain in the cytoplasm. Moreover, the nuclear diameter is determined with a greater degree of accuracy than with time-of-flight sizing methods, due to the dimension of the nucleus being small relative to beam width.

The two parameter distribution of particles such as those of FIG. 8 is represented by the depiction of FIG. 9, which represents a hard copy printout of an analysis device wherein the numbers and letters indicate the relative number of particles falling within each of the two parameters plotted. In FIG. 9, cell diameter from light scatter pulse width measurement is plotted on the vertical axis, increasing in size in a downward direction, while nuclear diameter from fluorescence pulse with rise time is plotted on the horizontal axis, increasing to the right. Two peaks are shown, as indicated by the circled symbols. This particular two parameter distribution represents results obtained from cultured human carcinoma (HEp-2) cells infected with herpes simplex virus type 2 (HSV-2). This distribution varies significantly from a similarly obtained distribution of normal cells, not shown herein. Further details may be found from the Leary, Todd, Wood and Jett article "Laser Flow Cytometric Light Scatter and Fluoroscence Pulse Width and Pulse Rise Time Sizing of Mammalian Cells" which is incorporated by reference hereinabove.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An analyzer adapted for connection to an output of a device of the type which conveys a particle through a beam of electromagnetic radiation and which responds to radiation resulting from interaction of the particle with the beam to output a resultant signal in the form of a pulse as the particle enters and passes through the beam, said analyzer serving to determine a dimensional attribute of the particle and comprising:
   means for measuring pulse edge width between two threshold values on at least one edge of the pulse as an indication of the particle attribute.

2. An analyzer according to claim 1, which includes means for establishing the two thresholds at constant fractions of the peak amplitude of the pulse.

3. An analyzer according to claim 2, wherein the particle attribute is the rate at which particle cross-sectional area changes along the particle in the direction of particle travel.

4. Apparatus for determining an attribute of a particle, said apparatus comprising:
   means for conveying the particle through a beam of electromagnetic radiation;
   means responsive to radiation resulting from interaction of the particle with the beam to output a resultant signal in the form of a pulse as the particle enters and passes through the beam;
   means for measuring pulse edge width between two threshold values on at least one edge of the pulse as an indication of the particle attribute.

5. Apparatus according to claim 4, which includes means for establishing the two thresholds at constant fractions of the peak amplitude of the pulse.

6. Apparatus according to claim 4, wherein the particle attribute is the rate at which particle cross-sectional area changes along the particle in the direction of particle travel.

7. Apparatus according to claim 5, wherein the particle attribute is the rate at which particle cross-sectional area changes along the particle in the direction of particle travel.

8. Apparatus according to claim 4, wherein the particle is fluorescent and the radiation resulting from interaction of the particle with the beam is secondary fluorescence.

9. Apparatus according to claim 5, wherein the particle is fluorescent and the radiation resulting from interaction of the particle with the beam is secondary fluorescence.

10. Apparatus according to claim 4, wherein the radiation resulting from interaction of the particle with the beam is scattered light.

11. Apparatus according to claim 5, wherein the radiation resulting from interaction of the particle with the beam is scattered light.

12. Apparatus according to claim 4, wherein the particle is a biological particle.

13. Apparatus according to claim 5, wherein the particle is a biological particle.

14. Apparatus according to claim 11, wherein the particle is a biological particle.

15. Apparatus according to claim 4, wherein the beam of electromagnetic radiation has a dimension in the direction of particle travel in the order of or less than the dimension of the particle in the direction of travel.

16. Apparatus according to claim 4, wherein the beam of electromagnetic radiation has a dimension in the direction of particle travel larger than the dimension of the particle in the direction of travel.

17. Apparatus according to claim 15, wherein at least one edge of the beam has an approximately Gaussian intensity distribution profile.

18. Apparatus according to claim 16, wherein at least one edge of the beam has an approximately Gaussian intensity distribution profile.

19. Apparatus according to claim 17, wherein the pulse edge characteristic is measured on a portion of the pulse which results from interaction of the particle with the beam near an outer edge thereof.

20. Apparatus according to claim 18, wherein the pulse edge characteristic is measured on a portion of the pulse which results from interaction of the particle with the beam near an outer edge thereof.

21. Apparatus according to claim 5, wherein the beam has an approximately Gaussian intensity distribution and lower and upper thresholds are respectively set at approximately 5% and 35% of the peak amplitude of the pulse.

22. Apparatus for obtaining orientation information for an asymmetrically-shaped particle being conveyed through a beam of electromagnetic radiation, said apparatus comprising:
means responsive to radiation resulting from interaction of the particle with the beam to generate a signal in the form of a pulse as the particle enters and passes through the beam;
first measurement means for measuring a characteristic of at least one edge of the pulse on a predetermined portion of the pulse edge, the pulse edge characteristic so measured being an indicator of the curvature of the portion of the particle which is first entering or last exiting the beam, depending upon whether said one edge of the pulse is the leading or the trailing edge;
second measurement means for independently measuring another characteristic of the pulse to obtain an independent indication of particle size; and
means responsive to the pulse edge characteristic measurement and to the other pulse characteristic measurement for correlating said measurements to yield orientation information.

23. Apparatus according to claim 22, wherein the other pulse characteristic is overall pulse width between two thresholds.

24. A method for analyzing the output pulse from a device of the type which conveys a particle through a beam of electromagnetic radiation and which responds to radiation resulting from interaction of the particle with the beam to output a resultant radiation intensity signal in the form of a pulse as the particle enters and passes through the beam, said method comprising:
measuring pulse edge width between two threshold values on at least one edge of the pulse as an indication of a particle attribute.

25. A method according to claim 24, which further comprises the step of establishing the two thresholds at constant fractions of the amplitude of the pulse.

26. A method according to claim 24, wherein the particle attribute is the rate at which particle cross-sectional area changes along the particle in the direction of particle travel.

27. An analyzer adapted for connection to an output of a device of the type which conveys a particle through a beam of electromagnetic radiation and which responds to radiation resulting from interaction of the particle with the beam to output a resultant signal in the form of a pulse as the particle enters and passes through the beam, said analyzer serving to determine an attribute of the particle and comprising:
means for measuring a characteristic of at least one edge of the pulse on a normalized basis with reference to peak pulse amplitude.

28. An analyzer according to claim 27, wherein said means for measuring measures the pulse edge characteristic on a predetermined portion of the pulse edge.

29. An analyzer according to claim 28, wherein the predetermined portion of the pulse edge is established as a function of peak pulse amplitude.

30. Apparatus for determining an attribute of a particle, said apparatus comprising:
means for conveying the particle through a beam of electromagnetic radiation;
means responsive to radiation resulting from interaction of the particle with the beam to output a resultant signal in the form of a pulse as the particle enters and passes through the beam; and
means for measuring a characteristic of at least one edge of the pulse on a normalized basis with reference to peak pulse amplitude.

31. An analyzer according to claim 30, wherein said means for measuring measures the pulse edge characteristic on a predetermined portion of the pulse edge.

32. An analyzer according to claim 31, wherein the predetermined portion of the pulse edge is established as a function of peak pulse amplitude.

33. Apparatus according to claim 30, wherein the beam of electromagnetic radiation has a dimension in the direction of particle travel in the order of or less than the dimension of the particle in the direction of travel.

34. Apparatus according to claim 30, wherein the beam of electromagnetic radiation has a dimension in the direction of particle travel larger than the dimension of the particle in the direction of travel.

35. Apparatus according to claim 33, wherein at least one edge of the beam has an approximately Gaussian intensity distribution profile.

36. Apparatus according to claim 34, wherein at least one edge of the beam has an approximately Gaussian intensity distribution profile.

37. Apparatus according to claim 35, wherein the pulse edge characteristic is measured on a portion of the pulse which results from interaction of the particle with the beam near an outer edge thereof.

38. Apparatus according to claim 36, wherein the pulse edge characteristic is measured on a portion of the pulse which results from interaction of the particle with the beam near an outer edge thereof.

39. A method for analyzing the output pulse from a device of the type which conveys a particle through a beam of electromagnetic radiation and which responds to radiation resulting from interaction of the particle with the beam to output a resultant radiation intensity signal in the form of a pulse as the particle enters and passes through the beam, said method comprising:

measuring a characteristic of at least one edge of the pulse on a normalized basis with reference to peak pulse amplitude to provide an indication of a particle attribute.

40. A method according to claim 39, wherein the pulse edge characteristic is measured on a predetermined portion of the pulse edge.

41. A method according to claim 40, wherein the predetermined portion of the pulse edge is established as a function of peak pulse amplitude.

* * * * *